United States Patent
Nussbaumer

[11] Patent Number: 5,990,116
[45] Date of Patent: Nov. 23, 1999

[54] TRISUBSTITUTED PHENYL DERIVATIVES

[75] Inventor: Peter Nussbaumer, Maria Enzersdorf, Austria

[73] Assignee: Novartis AG, Basel, Switzerland

[21] Appl. No.: 08/913,597

[22] PCT Filed: Mar. 14, 1996

[86] PCT No.: PCT/EP96/01116

§ 371 Date: Sep. 15, 1997

§ 102(e) Date: Sep. 15, 1997

[87] PCT Pub. No.: WO96/28430

PCT Pub. Date: Sep. 19, 1996

[30] Foreign Application Priority Data

Mar. 14, 1995 [GB] United Kingdom ............ 9505080
Mar. 23, 1995 [GB] United Kingdom ............ 9505858
Dec. 28, 1995 [GB] United Kingdom ............ 9526593

[51] Int. Cl.$^6$ ............ A61K 31/505; C07D 239/88; C07D 239/93; C07D 239/94

[52] U.S. Cl. ............ 514/259; 544/283; 544/287; 544/293; 546/152; 546/153; 546/156; 546/159; 546/168; 546/170; 546/171; 546/178; 560/45; 564/167; 564/443; 514/311; 514/312; 514/313; 514/619; 514/630; 514/646

[58] Field of Search ............ 544/283, 287, 544/293; 514/259

[56] References Cited

U.S. PATENT DOCUMENTS

| | | | |
|---|---|---|---|
| 4,851,423 | 7/1989 | Girijavallabhan et al. | 514/399 |
| 5,272,167 | 12/1993 | Girijavallabhan et al. | 514/394 |
| 5,409,930 | 4/1995 | Spada et al. | 514/248 |
| 5,459,144 | 10/1995 | Girijavallabhan et al. | 514/269 |
| 5,480,883 | 1/1996 | Spada et al. | 514/249 |
| 5,646,153 | 7/1997 | Spada et al. | 514/259 |
| 5,656,643 | 8/1997 | Spada et al. | 514/312 |

FOREIGN PATENT DOCUMENTS

| | | |
|---|---|---|
| 0028305 A1 | 5/1981 | European Pat. Off. . |
| 0081782 | 6/1983 | European Pat. Off. . |
| 0181568 | 5/1986 | European Pat. Off. . |
| 0274867 A2 | 7/1988 | European Pat. Off. . |
| 0274867 B1 | 7/1988 | European Pat. Off. . |
| 0407217 A1 | 1/1991 | European Pat. Off. . |
| 0497740 A1 | 8/1992 | European Pat. Off. . |
| 0539326 A2 | 4/1993 | European Pat. Off. . |
| 0560407 B1 | 9/1993 | European Pat. Off. . |
| 0584222 B1 | 3/1994 | European Pat. Off. . |
| 88/03800 | 6/1988 | WIPO . |
| 88/03806 | 6/1988 | WIPO . |
| 92/20642 | 11/1992 | WIPO . |

OTHER PUBLICATIONS

Derwent Abstract: Japan Tobacco, 97–415263/38.

Nagpal et al., "New Dermatological Agents for the Treatment of Psoriasis," Annual Reports in Medicinal Chemistry, vol. 32, Ch. 20, pp. 201–210, 1997.

Goodman & Gilman's, "The Parmacological Basis of Therapeutics," Academic Press, Ninth Edition, Ch. 64, pp. 1607–1608, 1996.

*Primary Examiner*—Richard L. Raymond
*Assistant Examiner*—Ann M. Kessinger
*Attorney, Agent, or Firm*—Carol A. Loeschorn

[57] ABSTRACT

The invention concerns compounds of formula I

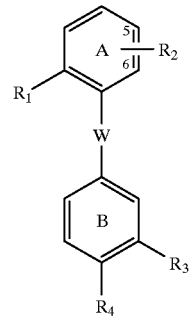

wherein the substituents have various meanings, and their use in the prevention or treatment of inflammatory and proliferative skin diseases and cancer.

11 Claims, No Drawings

TRISUBSTITUTED PHENYL DERIVATIVES

The present invention concerns new organic compounds, processes for their production, pharmaceutical compositions containing them and their use as pharmaceuticals especially for the treatment of proliferative and/or inflammatory disorders and cancer.

More particularly the invention concerns compounds of the formula

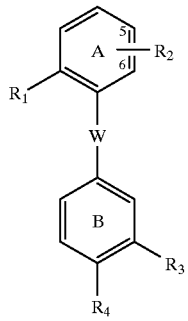

I wherein $R_1$ and $R_2$ are the same or different and represent hydroxy, alkoxy, acyloxy, alkyl or acyl, whereby $R_2$ is in the 5- or 6-position, with the proviso that $R_1$ and $R_2$ are not simultaneously hydroxy or acyloxy, and a) W represents —$CH_2CH_2$—, $R_3$ represents a group of formula

wherein $R_6$ represents hydrogen, alkyl, alkoxy or amino and X represents oxygen, hydroxyimino or alkoxyimino, $R_4$ represents a group of formula

wherein $R_7$ and $R_8$ are the same or different and represent hydrogen, alkyl, acyl or alkoxycarbonyl, or b) W represents —$CH_2CH_2$—, —$CH$=$CH$—, —$CH_2O$— or —$CH_2NR_5$—, whereby the heteroatom adheres to ring B and $R_5$ represents hydrogen, alkyl or acyl, $R_3$ and $R_4$ form together with the adjacent ring B a condensed ring system of formula

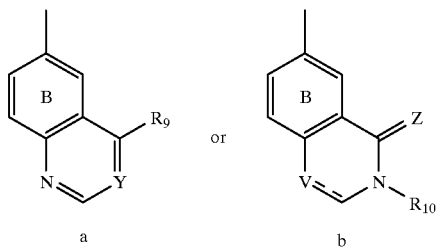

wherein the symbol ==== represents a single or a double bond, $R_9$ represents hydrogen, alkylthio, alkyl, alkoxycarbonyl, acyl, amino, acylamino, diacylamino, alkylamino, dialkylamino, cyano, hydroxy, alkoxy or mercapto, Y represents N or $CR_{11}$, $R_{10}$ represents hydrogen, alkyl, acyl or optionally substituted phenylalkyl, $R_{11}$ represents hydrogen, alkoxycarbonyl, cyano or acyl, Z represents O or S and V represents NH, if the symbol ==== represents a single bond, and N, if the symbol ==== represents a double bond, with the proviso that, if $R_9$ represents hydroxy or mercapto and Y represents N, the compounds exist predominantly in the tautomeric form of formula

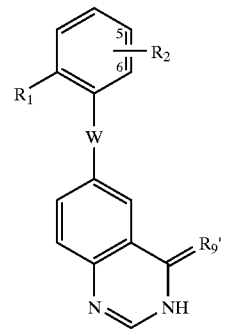

It wherein $R_9'$ represents O or S, in free form or, where such forms exist, in salt form, herein briefly named "compounds of the invention".

The compounds of the invention possess interesting pharmacological, in particular antiproliferative, antiinflammatory and antitumor activity.

Alkyl as such or as part of a substituent such as alkoxy preferably is of 1 to 4 carbon atoms, it particularly is methyl or ethyl. Acyl preferably is the residue of a carboxylic acid, in particular an alkyl, arylalkyl or aryl carboxylic acid, whereby aryl preferably is phenyl, and the alkylene part of acyl, including the carbonyl group, preferably is of 1 to 5 carbon atoms. A preferred acyl moiety is acetyl.

In a preferred group of compounds of the invention $R_1$ and $R_2$ independently are alkoxy of 1 to 4 carbon atoms, W represents —$CH_2CH_2$— and $R_3$ and $R_4$ represent a condensed ring system as defined above.

A preferred group are compounds of formula

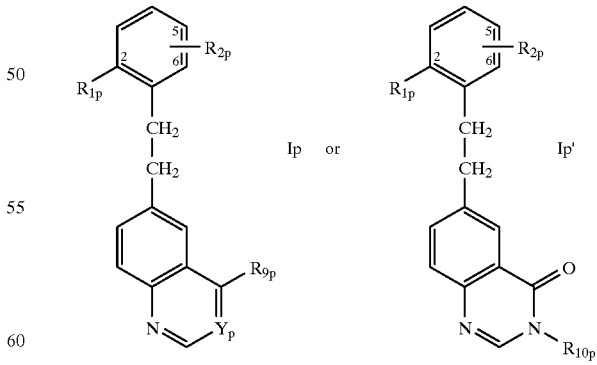

wherein $R_{1p}$ and $R_{2p}$ are the same or different and represent hydroxy, alkoxy, acyloxy, alkyl or acyl, whereby $R_{2p}$ is in the 5- or 6-position, with the proviso that $R_{1p}$ and $R_{2p}$ are not simultaneously hydroxy or acyloxy, $R_{9p}$ represents hydrogen, alkyl, alkoxycarbonyl, acyl, amino, acylamino, diacylamino, alkylamino, dialkylamino, cyano, alkoxy or hydroxy, $Y_p$ represents N or CH and $R_{10p}$ represents hydrogen, alkyl or acyl, with the proviso that, if $R_{9p}$ represents hydroxy and $Y_p$ represents N, the compounds exist predominantly in the tautomeric form of formula

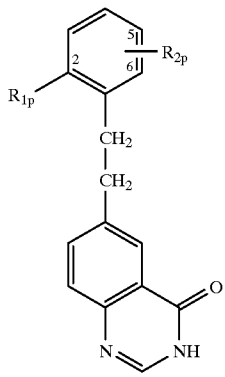

Ip' in free form, or where such forms exist, in salt form.

A further preferred group are compounds of formula

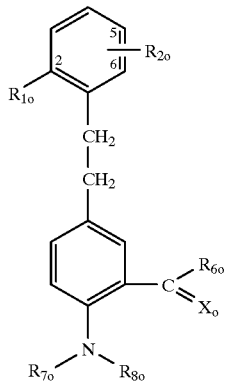

Io wherein $R_{1o}$ and $R_{2o}$ are the same or different and represent alkyl, acyl or alkoxy, and $R_{6o}$, $R_{7o}$, $R_{8o}$ and $X_o$ have the same significance as $R_6$, $R_7$, $R_8$ and X, in free form or, where such forms exist, in salt form.

Unless otherwise stated alkyl moieties are preferably straight or branched chains having 1 to 12, especially 1 to 8 carbon atoms, particularly 1 to 6 and expecially 1 to 4. Any lower alkyl present as or in a substituent is straight or branched-chain and has preferably 1 to 4, especially 1 or 2 carbon atoms.

A further preferred group of compounds of the invention is the compounds of formula

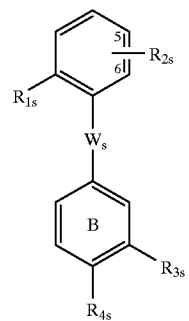

Is wherein $R_{1s}$ is hydroxy, alkyl of 1 to 4 carbon atoms or alkoxy of 1 to 4 carbon atoms;

$R_{2s}$ is hydroxy or alkoxy of 1 to 4 carbon atoms and is in the 5- or 6-position, whereby $R_{1s}$ and $R_{2s}$ are not simultaneously hydroxy; and a) $W_s$ is —$CH_2CH_2$—;

$R_{3s}$ is a group of formula —$COR_{6s}$ wherein $R_{6s}$ is alkyl of 1 to 4 carbon atoms, alkoxy of 1 to 4 carbon atoms, or amino; and $R_{4s}$ is amino, alkylamino of 1 to 4 carbon atoms, dialkylamino independently of 1 to 4 carbon atoms in each alkyl part thereof, alkylcarbonylamino of 1 to 4 carbon atoms in the alkyl part thereof, or alkoxycarbonylamino of 1 to 4 carbon atoms in the alkoxy part thereof; or b) $W_s$ is —$CH_2CH_2$—, —$CH_2NH$—, —$CH_2O$— or —$CH=CH$—, whereby the nitrogen or oxygen atom is bound to ring B; and $R_{3s}$ and $R_{4s}$ together with ring B form a condensed ring system of formula

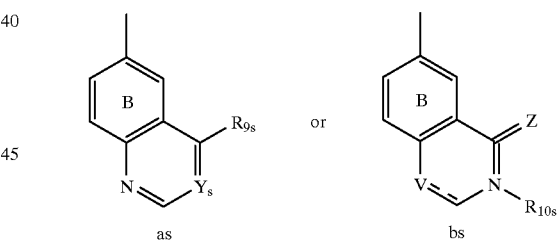

as    bs wherein the symbol ==== is a single or a double bond;

$R_{9s}$ is hydrogen, alkylthio of 1 to 4 carbon atoms, alkyl of 1 to 4 carbon atoms, amino, diacetylamino, alkylamino of 1 to 4 carbon atoms, hydroxy, alkoxy of 1 to 4 carbon atoms or mercapto;

$Y_s$ is N or $CR_{11s}$ wherein $R_{11s}$ is hydrogen or alkoxycarbonyl of 1 to 4 carbon atoms in the alkoxy part thereof, $R_{10s}$ is hydrogen, alkyl of 1 to 4 carbon atoms or dialkoxybenzyl independently of 1 to 4 carbon atoms in the alkoxy parts thereof; and Z and V are as defined above;

with the proviso that, if $R_{9s}$ is hydroxy or mercapto and $Y_s$ is N, then the compounds exist predominantly in the tautomeric form of formula

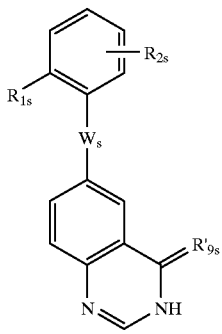

wherein R'$_{9s}$ is O or S,
in free form or, where such forms exist, in salt form.

An even further preferred group of compounds of the invention is the compounds of formula Iss

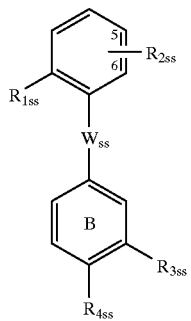

wherein
R$_{1ss}$ is hydroxy, alkyl of 1 or 2 carbon atoms or alkoxy of 1 or 2 carbon atoms;
R$_{2ss}$ is hydroxy or alkoxy of 1 or 2 carbon atoms and is in the 5- or 6-position, whereby R$_{1ss}$ and R$_{2ss}$ are not simultaneously hydroxy;
W$_{ss}$ is —CH$_2$CH$_2$—, —CH$_2$NH—, —CH$_2$O— or —CH=CH—, whereby the nitrogen or oxygen atom is bound to ring B; and
R$_{3ss}$ and R$_{4ss}$ together with ring B form a condensed ring system of formula

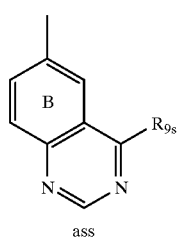

Its

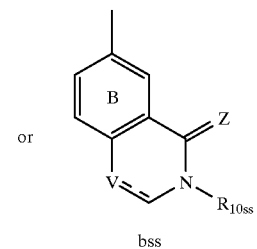

or

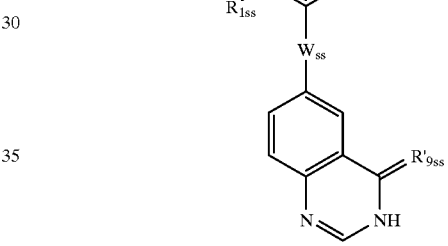

bss the symbol ==== is a single or a double bond;
R$_{9s}$ is as defined above;
R$_{10ss}$ is hydrogen, methyl, 2,5-dimethoxybenzyl or 2,6-dimethoxybenzyl; and
Z and V are as defined above;

whereby, if R$_{9s}$ is hydroxy or mercapto, then the compounds exist predominantly in the tautomeric form of formula Itss wherein R$_{1ss}$ and R$_{2ss}$ are as defined above and R'$_{9ss}$ is oxygen or sulfur, in free form or, where such forms exist, in salt form.

In a subgroup of compounds of formula Iss R$_{1ss}$ is methoxy or ethoxy. In a further subgroup thereof R$_{2ss}$ is methoxy or ethoxy. In a further subgroup thereof W$_{ss}$ is —CH$_2$CH$_2$—. In a further subgroup thereof R$_{3ss}$ and R$_{4ss}$ together with ring B form a condensed ring system of formula ass or bss wherein R$_{9s}$ is alkyl or alkoxy, each of 1 to 4 carbon atoms; R$_{10ss}$ is hydrogen, methyl or 2,5- or 2,6-dimethoxybenzyl; Z is O; and V is N and the symbol ==== represents a double bond.

The present invention also provides processes for the preparation of compounds of formula 1, comprising a) for the preparation of compounds of formula Ia and Ib

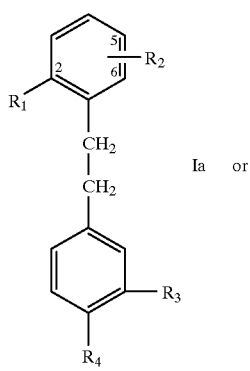 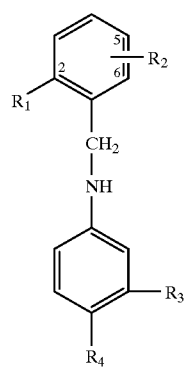

Ia or Ib

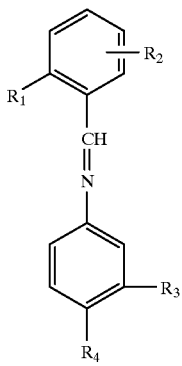

IIc wherein the substituents are as defined above, reducing a compound of formula IIa, IIb or IIc wherein the substituents are as defined above, in conventional manner or b) for the preparation of compounds of formula

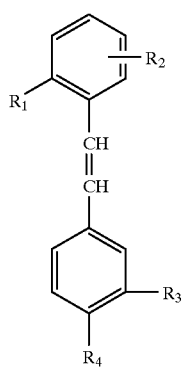

IIa

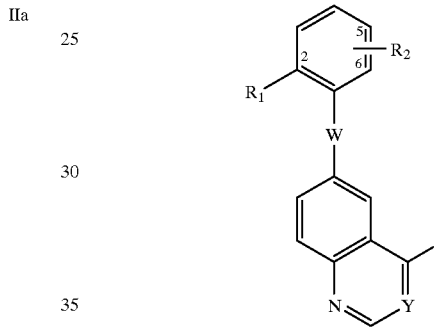

Ic or

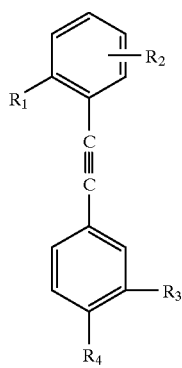

IIb and

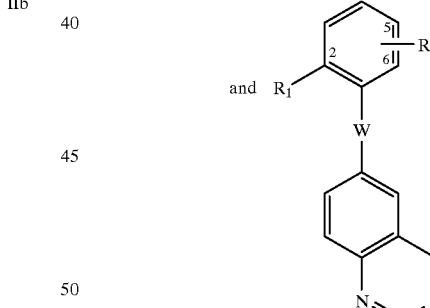

Id or wherein $R_9''$ is hydrogen, hydroxy or alkyl and the other substituents are as defined above, ring closure of the heterocycle of the bicyclic ring system starting from monocyclic precursors of formula

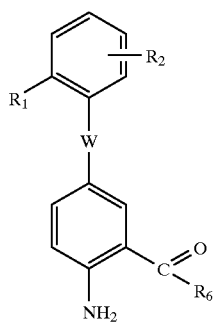

IIIa or

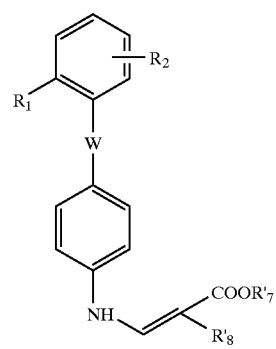

IIIb wherein R'₇ represents alkyl and R'₈ represents alkoxycarbonyl, cyano or acyl, and the other substituents are as defined above, according to known methods for the preparation of quinolines and quinazolines, or c) for producing compounds of formula Ie

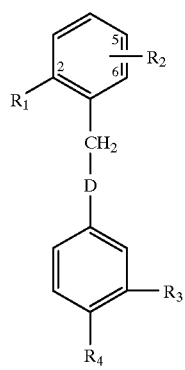

wherein the substituents are as defined above and D represents O or $NR_5$, reacting a compound of formula

IV

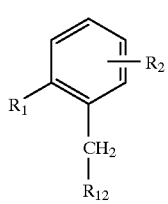

wherein $R_{12}$ represents a leaving group, with a compound of formula

V

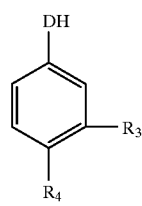

wherein the substituents are as defined above, or d) for producing compounds of formula If

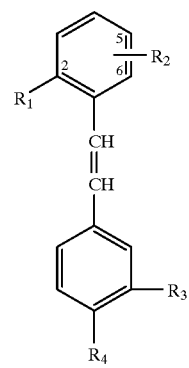

wherein the substituents are as defined above, coupling a compound of formula

VI

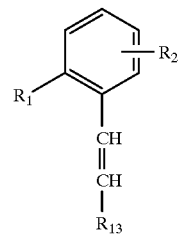

wherein $R_{13}$ represents a Sn(alkyl)₃-group or a B($R_{14}$)₂-group, whereby $R_{14}$ represents alkyl, cycloalkyl, alkoxy or aryloxy or the two substituents may form together with the boron atom a cyclic structure derived from 9-borabicyclononane or catecholborane, and the rest of the substituents are as defined above, with a compound of formula

VII

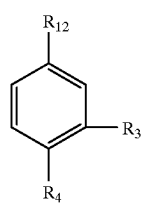

wherein the substituents are as defined above, or e) for the preparation of compounds of formula I starting from different compounds of formula I, by functional group transformation, such as ester, amide and ether cleavage, acylation and alkylation of hydroxy or amino functions, decarboxylation or by chemical manipulation of the heterocyclic ring system, such as reduction of or addition to —C=N— bonds, whereby in these reactions functional groups may be protected by suitable protecting groups; which may be removed subsequent to the reaction in conventional manner, and recovering thus obtained compounds of formula I in free form or, where such forms exist, in salt form.

Process a) may be performed following standard procedures for hydrogenation of double or triple bonds, preferably using hydrogen in combination with hydrogenation catalysts, such as Pd, Pt or Rh, most preferably Pd on charcoal and, for reducing a Schiff-base (formula IIc) using a complex metal hydride, such as sodium cyanoborohydride, in an inert solvent, e.g. an alcohol.

Process b) is performed according to standard reactions for the synthesis of heterocycles fused to a benzene ring starting from appropriately substituted benzene derivatives.

Process c) is performed according to standard procedures for 0- and N-alkylation using benzyl halogenides, -sulfates or -mesylates, preferably benzylbromides, in the presence of a suitable base, preferably alkali carbonates or alkali hydrides, in an inert and preferably polar solvent, such as acetone or dimethylformamide, at temperatures between −20 and 120° C., preferably between room temperature and 60° C.

Process d) is performed according to standard procedures for the coupling of vinylstannanes (Stille coupling) or vinylboranes, preferably prepared by addition of boronhydrides to alkynes of formula VIIIb with arylhalogenides, preferably aryliodides and arylbromides, under transition metal catalysis, preferably using palladium catalysts.

The starting material of formula IIa may be prepared reacting a compound of formula

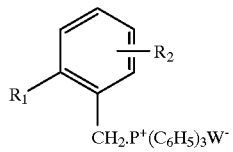

VIII with a compound of formula

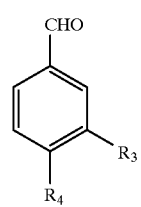

IX or reacting a compound of formula

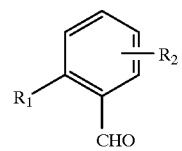

VIIIa with a compound of formula

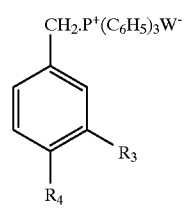

IXa wherein the substituents are as defined above and W⁻ represents an anion, preferably bromide. This process may be carried out in a manner conventional for Wittig/Horner/Emmons type reactions by treatment of the phosphor component with a base, such as an alkyl lithium, an alkali hydride or an alkali amide, e.g. sodium amide, lithium diisopropylamide, or an alkali alcoholate, at a temperature between −70° C. and 100° C. and simultaneous or subsequent conversion with the carbonyl component at temperatures between −70° and 120° C., preferably −60° to 60° C., in appropriate solvents, such as, for example, tetrahydrofuran, toluene or dimethylsulfoxide.

The starting material of formula IIb may be prepared reacting a compound of formula

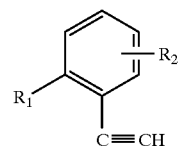

VIIIb with a compound of formula

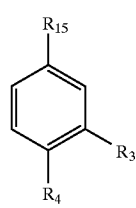

IXb wherein the substituents are as defined above and $R_{15}$ represents halogen, preferably iodine, following standard procedures for the Heck reaction of haloolefines with acetylenes.

The starting compounds of formula III can be prepared analogously as described for the compounds of formula I.

The other starting materials and intermediate compounds are either known or can be prepared according to known methods or analogously as described in the examples.

In the following examples, which illustrate the invention but in no way limit its scope, references to temperature are in degrees celsius.

EXAMPLE 1

5-[2-(2,5-Dimethoxyphenyl)ethyl]-2-Acetylamino Benzoic Acid Methylester (Process a)

150 mg of 5-[2-(2,5-dimethoxyphenyl)ethenyl]-2-acetylamino benzoic acid methylester are dissolved in 10 ml of ethyl acetate. After addition of 25 mg of palladium (10% on charcoal) the mixture is stirred overnight under an atmosphere of hydrogen and filtered over celite. The filtrate is evaporated in vacuo to obtain the title compound as colourless crystals. mp:81–83°.

Analogously as described in example 1 the following compounds of formula A

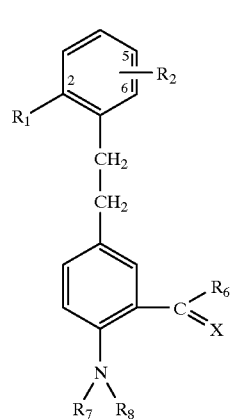

A are obtained:

| Ex.: | $R_1$ | $R_2$ | $R_8$ | $R_7$ | $R_8$ | X | m.p.: |
|---|---|---|---|---|---|---|---|
| 2 | $OCH_3$ | 5-$OCH_3$ | O-nBu | Ac | H | 0 | 58° |
| 3 | " | 6-$OCH_3$ | $OCH_3$ | Ac | H | 0 | 108° |
| 4 | " | 5-$OCH_3$ | $CH_3$ | H | H | 0 | oil |
| 5 | " | " | $NH_2$ | H | H | 0 | 112° |

EXAMPLE 6

6-[2-(2,5-Dimethoxyphenyl)ethyl]-4-ethyl-quinazoline (Process a)

150 mg of 6-[2-(2,5-dimethoxyphenyl)ethynyl]-4-ethyl-quinazoline are dissolved in 10 ml of ethyl acetate. After addition of 20 mg of palladium (10% on charcoal) the mixture is stirred overnight under an atmosphere of hydrogen and subsequently filtered over celite. The filtrate is evaporated in vacuo and the residue crystallised from cylohexane to obtain the title compound as colourless crystals. mp: 74°.

Analogously as described in example 6 the following compounds of formula B, C and D are obtained:

| Ex: | form | W | $R_1$ | $R_2$ | Y | $R_9$ | Z | $R_{10}$ | m.p.: |
|---|---|---|---|---|---|---|---|---|---|
| 7 | C | —$CH_2CH_2$— | $OCH_3$ | 5-$OCH_3$ | — | — | O | H | 157° |
| 8 | B | " | " | " | N | $OC_2H_5$ | — | — | 80° |
| 9 | B | " | " | " | N | $NAc_2$ | — | — | 118° |
| 10 | B | " | " | 6-$OCH_3$ | N | $OCH_3$ | — | — | 133–135° |
| 11 | C | " | " | " | — | — | O | H | 198–201° |

-continued

| Ex: | form | W | R₁ | R₂ | Y | R₉ | Z | R₁₀ | m.p.: |
|---|---|---|---|---|---|---|---|---|---|
| 12 | B | " | OH | 5-OCH₃ | N | OCH₃ | — | — | 176–180° |
| 13 | B | " | OCH₃ | " | N | NHCH₃ | — | — | 147–150° |
| 14 | B | " | " | 5-OH | N | OCH₃ | — | — | 174–176° |
| 15 | B | " | " | 5-OCH₃ | N | H | — | — | 78–80° |
| 16 | B | " | " | " | N | OCH₃ | — | — | 62° |
| 17 | B | " | " | " | N | CH₃ | — | — | 70° |
| 18 | B | " | OC₂H₅ | 5-OC₂H₅ | N | C₂H₅ | — | — | 80° |
| 19 | B | " | C₂H₅ | 5-C₂H₅ | N | " | — | — | 42° |
| 20 | B | " | OCH₃ | 6-OCH₃ | N | " | — | — | 104–108° |

EXAMPLE 21

6-(2,5-Dimethoxybenzylamino)-3H-quinazolin-4-one (Process a)

A mixture of 200 mg of 6-amino-3H-quinazolin-4-one and 206 mg of 2,5-dimethoxybenzaldehyde in 12 ml of dry methanol is heated to 60° for 16 hours. cooling the yellow precipitate is filtered and resuspended in 10 ml of dry methanol. This mixture is treated with 85 mg of sodium cyanoborohydride and heated for some minutes until all the materials are dissolved. After stirring for 2 at room temperature, the mixture is poured into water and extracted with acetate. The combined organic extracts are dried over magnesium sulfate and evaporated in vacuo. The pure title compound is obtained by crystallisation from ethanol as colourless crystals. mp: 203–205°.

EXAMPLE 22

[2,5-Dimethoxyphenyl)ethyl]-4-hydroxy-3-quinolinecarboxylic Acid Ethylester (Process b)

1.48 g of diethyl {4-[2-(2,5-dimethoxyphenyl)ethyl]anilino}methylene-malonate are dissolved in 20 ml of warm diphenylether and heated to reflux for 30 minutes. The cold mixture is diluted with pentane, and the precipitate collected and dissolved in dichloromethane. The solution is dried over magnesium sulfate, and the solvent distilled off. The residue is cristallysed from isopropanol to afford the title compound as yellowish crystals. mp: 195–198°.

EXAMPLE 23

6-(2,5-Dimethoxybenzyloxy)-3H-quinazolin-4-one (Process b)

90 mg of 5-(2,5-dimethoxybenzyloxy)-2-formylaminobenzamide are heated without solvent in a Kugelrohr apparatus at 170° for 1 hour. The resulting solid is purified by silica gel chromatography (ethyl acetate) to give colourless crystals. mp: 155–158°.

EXAMPLE 24

3-(2,6-Dimethoxybenzyl)-6-(2,5-dimethoxybenzyloxy)-3H-quinazolin-one (process c)

12 mg of sodium hydride (80% in mineral oil) are added to a solution of 115 mg of 3-(2,6-dimethoxybenzyl)-6-hydroxy-3H-quinazolin-4-one in 10 ml of dry dimethylformamide. After stirring for 30 minutes at room temperature, 85 mg of 2,5-dimethoxybenzylbromide are added, and stirring is continued overnight. The solvent is distilled off in vacuo, and the residue partitioned between aqueous pH7-buffer solution and ethyl acetate. The organic phase is separated, dried over magnesium sulfate and evaporated in vacuo. The pure title compound is obtained after silica gel chromatography (toluene/ethyl acetate=2/1) as colourless crystals. mp: 148–150°.

Analogously as described in example 24 the following compounds of formula B and C are obtained:

| Ex. | form | W | R₁ | R₂ | Z | R₁₀ | Y | R₉ | m.p. |
|---|---|---|---|---|---|---|---|---|---|
| 25 | C | —CH₂O— | OCH₃ | 5-OCH₃ | O | 2,5-DMB | — | — | 92° |
| 26 | C | —CH₂O— | OCH₃ | 6-OCH₃ | O | 2,6-DMB | — | — | 167–170° |
| 27 | B | —CH₂O— | OCH₃ | 6-OCH₃ | — | — | N | OCH₃ | 170–172° |

2,5-DMB = 2,5-dimethoxybenzyl
2,6-DMB = 2,6-dimethoxybenzyl

EXAMPLE 28

(E)-6-[2-(2,5-Dimethoxyphenyl)ethenyl)]4-methoxyquinazoline Process d)

At 0° under argon atmosphere, 500 mg of 2,5-dimethoxyphenylacetylene dissolved in 30 ml of dry tetrahydrofuran are treated with 450 mg of 9boranbicyclo [3.3.1]nonane. After stirring for 2 hours at room temperature, 650 mg of 6-iodo-4-methoxyquinazoline, 800 mg of potassium phosphate, 64 mg of tetrakishenylphosphine)palladium(0), and 15 ml of dioxane are added to the vinylborane intermediate. The mixture is stirred vigorously at 85° for 3 hours, then poured into water and extracted with ethyl acetate. The combined organic extracts are dried over magnesium sulfate and concentrated in vacuo. The residue is chromatographed on silica gel to give the title compound as yellowish oil.

$^1$H-NMR (CDCl₃): 8.77 (s ,1H); 8.19 (d, J=2 Hz, 1H); 8.10 (dd, J=2+8.8 Hz, 1H); 7.90 (d, J=8.8 Hz, 1H); 7.60 (d, J=16.5 Hz, 1H); 7.24 (d, J=16.5 Hz, 1H); 7.18 (d, J=2.4 Hz, 1H); 6.80–6.90 (m, 2H); 4.21 (s, 3H); 3.88 (s, 3H); 3.84 (s, 3H).

Analogously as described in example 28 the following compound of formula B is obtained:

| Ex. | W | $R_1$ | $R_2$ | Y | $R_9$ | m.p. |
|---|---|---|---|---|---|---|
| 29 | —CH=CH— (E) | $OCH_3$ | 5-$OCH_3$ | N | $C_2H_5$ | 105° |

EXAMPLE 30

6-[2-(2,5-Dimethoxyphenyl)ethyl]-3-methyl-4quinazolinone (Process e)

34 mg of 6-[2-(2,5-dimethoxyphenyl)ethyl]-4-quinazolinone are dissolved in 4 ml of dimethylformamide and treated with 4 mg of sodium hydride (80% in mineral oil). After stirring for 30 minutes, 0.1 ml of methyl iodide are added, and stirring is continued for 1 hour. The mixture is poured onto water and extracted with ethyl acetate. The combined organic layers are dried over magnesium sulfate and concentrated in vacuo. Silica gel chromatography (cyclohexane/ethyl acetate=1/2) of the residue gives the title compound as colourless crystals. mp: 83–85°.

Analogously as described in example 30 the following compounds of formula B and obtained:

| Ex | form | W | $R_1$ | $R_2$ | Y | $R_9$ | Z | $R_{10}$ | m.p. |
|---|---|---|---|---|---|---|---|---|---|
| 31 | C | —$CH_2CH_2$— | $OCH_3$ | 5-$OCH_3$ | — | — | O | 2,5-DMB | 78–80° |
| 32 | C | —$CH_2O$— | " | " | — | — | O | $CH_3$ | 150° |
| 33 | B | —$CH_2CH_2$— | " | " | —C= \| $COOC_2H_5$ | $OCH_3$ | — | — | 150–151° |
| 34 | C | " | " | 6-$OCH_3$ | — | — | O | 2,6-DMB | 140–142° |

EXAMPLE 35

6-[2-(2,5-Dimethoxyphenyl)ethyl]-2,3-dihydro-1H-quinazolin-4-one (Process e)

130 g of 6-[2-(2,5-dimethoxyphenyl)ethyl]-3H-quinazolin-4-one are dissolved in 3 ml of acetic acid and treated with 58 mg of sodium borohydride. After stirring for 5 hours at room temperature, the mixture is poured onto 2 M aqueous pH7 buffer solution and extracted with ethyl acetate. The combined organic layers are dried over magnesium sulfate and concentrated in vacuo. The residue is chromatographed on silica gel to give the title compound as colourless crystals. mp.: 138–140°.

Analogously as described in example 35 the following compound of formula D is obtained:

| Ex | W | $R_1$ | $R_2$ | Z | $R_{10}$ | m.p. |
|---|---|---|---|---|---|---|
| 36 | —$CH_2CH_2$— | $OCH_3$ | 5-$OCH_3$ | O | $CH_3$ | 110–112° |

EXAMPLE 37

4-Amino-6-[2-(2,5-dimethoxyphenyl)ethyl]-quinazoline (Process e)

A solution of 50 mg of 4-diacetylamino-6-[2-(2,5-dimethoxyphenyl)ethyl]-quinazoline and 10 ml of 1 N aqueous sodium hydroxide solution in dioxane is stirred for 3 hours at room temperature. The mixture is poured onto water and extracted with ethyl acetate. The combined organic extracts are dried over magnesium sulfate and concentrated in vacuo. The residue is taken up in methanol, stirred for 30 minutes, filtered and concentrated again. Chromatographic purification (silica gel, ethyl acetate) gives the title compound as colourless crystals. mp.: 160–165°.

EXAMPLE 38

6-[2-(2,5-Dimethoxyphenyl)ethyl]-4-isopropyloxyquinazoline (Process e)

150 mg of 6-[2-(2,5-dimethoxyphenyl)ethyl]-3H-quinazolin-4-one are heated together with 5 ml of phosphorus oxychloride and 100 mg of phosphorus pentachloride at reflux for 30 minutes. The mixture is concentrated in vacuo and then partitioned between ice-cold 2 M aqueous pH 7 buffer and ethyl acetate. The organic layer is separated, dried and evaporated in vacuo to yield crude 6-[2-(2,5-dimethoxyphenyl)ethyl]-4-chloroquinazoline, which can be directly used in the following step or purified by chromatography (silica gel, cyclohexane/ethyl acetate=1/1). The crude intermediate is added to a solution of sodium isopropoxide (prepared from 8.3 mg of sodium in 20 ml of isopropanol) in isopropanol. The mixture is refluxed for 1 hour, concentrated in vacuo and poured onto water. Extraction with ethyl acetate yields the crude title compound, which is purified by chromatography on silica gel (cyclohexane/ethyl acetate=2/1) to give a colourless oil.

$^1$H-NMR (CDCl$_3$): 8.73 (s, 1H); 7.92 (d, J=2 Hz, 1H); 7.82 (d, J=8.5 Hz, 1H); 7.66 (dd, J=2+8.5 Hz, 1H); 6.68–6.80 (m, 3H); 5.62 (sep, J=6.2 Hz, 1H); 3.77 (s, 3H); 3.71 (s, 3H); 2.91–3.1 (m, 4H); 1.47 (d, J=6.2 Hz, 6H).

Analogously as described in example 38 the following compounds of formula I are obtained:

| Ex | form | W | $R_1$ | $R_2$ | Y | $R_9$ | Z | $R_{10}$ | m.p.: |
|---|---|---|---|---|---|---|---|---|---|
| 39 | B | —$CH_2CH_2$— | $OCH_3$ | 5-$OCH_3$ | N | $SCH_3$ | — | — | 95° |
| 40 | C | " | " | " | — | — | S | H | 185–190° |

EXAMPLE 41

6-[2-(5-Hydroxy-2-methoxyphenyl)ethyl]-3H-quinazolin-4-one (process e)

90 mg of 6-[2-(5-hydroxy-2-methoxyphenyl)ethyl]-4-methoxyquinazoline are dissolved in 8 ml of methanol and treated with 1 ml of 4 N aqueous hydrochloric acid. The mixture is stirred for 16 hours at room temperature, then poured onto 2 M aqueous pH 7 buffer and extracted with ethyl acetate. The combined organic extracts are dried over magnesium sulfate and evaporated in vacuo. The residue is chromatographed on silica gel (dichloromethane/methanol=9/1) to yield the title compound as colourless crystals. mp: 221–224°.

EXAMPLE 42

5-[2-(2,5-Dimethoxyphenyl)ethyl]-2-methoxycarbonylamino Benzoic acid Methylester (Process e)

A mixture of 115 mg of 5-[2-(2,5-dimethoxyphenyl)ethyl]-2-amino benzoic acid methylester and 50 mg of 4-dimethylaminopyridine in 6 ml of dry dichloromethane is treated with 35 mg of methyl chloroformiate and stirred for 3 hours at room temperature. Then the mixture is poured onto aqueous pH7 buffer solution and extracted with ethyl acetate. The combined organic extracts are dried over magnesium sulfate and concentrated in vacuo. The crude product is purified by silica gel chromatography (cyclohexane/ethyl acetate=8/1) to yield the title compound as colourless crystals. mp: 80–82°.

EXAMPLE 43

5-[2-(2,5-Dimethoxyphenyl)ethyl]-2-methylamino Benzoic Acid Methylester (Process e)

110 mg of 5-[2-(2,5-dimethoxyphenyl)ethyl]-2-amino benzoic acid methylester are dissolved in 6 ml of dry dimethylformamide and treated with 13 mg of sodium hydride (80% in mineral oil). After stirring for 30 minutes at room temperature, 0.2 ml of methyl iodide are added and stirring continued overnight. The solvent is distilled off in vacuo, and the residue is partitioned between aqueous ph7 buffer solution and ethyl acetate. The separated organic layer is dried over magnesium sulfate and concentrated in vacuo. The residue is chromatographed on silica gel (hexane/ethyl acetate=7/1) to give the title compound as colourless crystals. mp: 73°.

Analogously as described in example 43 the following compound of formula A is obtained:

| Ex | $R_1$ | $R_2$ | $R_6$ | $R_7$ | $R_8$ | X | m.p. |
|---|---|---|---|---|---|---|---|
| 44 | $OCH_3$ | 5-$OCH_3$ | $OCH_3$ | $CH_3$ | $CH_3$ | O | oil |

EXAMPLE 45

5-[2-(2,5-Dimethoxyphenyl)ethyl]-2-acetylamino Benzoic Acid Ethylester (Process e)

A mixture of 93 mg of 5-[2-(2,5-dimethoxyphenyl)ethyl]-2-acetylamino-benzoic acid butylester, 100 mg of lithium bromide, 55 mg of 1,8-diazabicyclo[5.4.0]undec-7-en and 4 ml of dry ethanol is heated to reflux for 3 hours. After neutralisation with 0.1 N aqueous hydrochloric acid, the mixture is extracted with ethyl acetate. The combined organic extracts are dried over magnesium sulfate and concentrated in vacuo. The pure title compound is obtained by silica gel chromatography (hexane/ethyl acetate=6/1) as colourless crystals. mp: 93°.

Analogously as described in example 45 the following compound of formula A is obtained:

| Ex | $R_1$ | $R_2$ | $R_6$ | $R_7$ | $R_8$ | X | m.p. |
|---|---|---|---|---|---|---|---|
| 46 | $OCH_3$ | 6-$OCH_3$ | $OC_2H_5$ | Ac | H | O | 87–90° |

Analogously as described in example 45 the following compound of formula B is obtained:

| Ex | W | $R_1$ | $R_2$ | Y | $R_9$ | m.p. |
|---|---|---|---|---|---|---|
| 47 | $CH_2CH_2$ | $OCH_3$ | 5-$OCH_3$ | $=C(COOCH_3)-$ | OH | 189–193° |

EXAMPLE 48

5-[2-(2,5-Dimethoxyphenyl)ethyl]-2-amino Benzoic Acid Methylester (Process e)

87 mg of 5-[2-(2,5-dimethoxyphenyl)ethyl]-2-acetylamino benzoic acid methylester are dissolved in 6 ml of methanol, treated with 1 ml of 4 N hydrochloric acid and stirred for 48 hours at room temperature. The mixture is neutralised by addition of 2 N aqueous sodium hydroxide solution and extracted with ethyl acetate. The combined organic layers are dried over magnesium sulfate and concentrated in vacuo. Purification by chromatography on silica gel (hexane/ethyl acetate=6/1) yields the title compound as colourless crystals. mp: 50–55°.

Analogously as described in example 48 the following compounds of formula A are obtained:

| Ex | $R_1$ | $R_2$ | $R_6$ | $R_7$ | $R_8$ | X | m.p. |
|---|---|---|---|---|---|---|---|
| 49 | $OCH_3$ | 6-$OCH_3$ | $OC_2H_5$ | H | H | O | 53–55° |
| 50 | " | 5-$OCH_3$ | " | H | H | O | oil |
| 51 | " | 6-$OCH_3$ | $OCH_3$ | H | H | O | 90–93° |

EXAMPLE 52

6-[2-(2,5-Dimethoxyphenyl)ethyl]-4-hydroxy-quinoline (Process e)

a) 300 mg of 6-[2-(2,5-dimethoxyphenyl)ethyl]-4-hydroxy-3-quinolinecarboxylic acid ethylester are dissolved in 10 ml of methanol, treated with 6 ml of 10% aqueous potassium hydroxide solution and heated to reflux for 2 hours. The mixture is poured onto 1 N hydrochloric acid and extracted with dichloromethane containing 3% of ethanol. The organic layers are dried over magnesium sulfate and evaporation of the solvent yields the corresponding free carboxylic acid as colourless crystals. mp: 148–151°.

b) 150 g of 6-[2-(2,5-dimethoxyphenyl)ethyl]-4-hydroxy-3-quinolinecarboxylic acid are dissolved in hot diphenylether, and the solution is heated to reflux for 1 hour. The cold reaction mixture is diluted with ethyl acetate and extracted with 6 N hydrochloric acid. The acidic aqueous layers are combined, washed with ethyl and then neutralised (pH 7) using aqueous ammonium hydroxide solution.

Extraction with ethyl actetate, drying over magnesium sulfate and evaporation yields a crude product, which is purified by chromatography on silica gel (dichloromethane/methanol=95/5) to give the title compound as yellowish crystals. mp: 141–145°.

Analogously as described in example 52 the following compound of formula B is obtained:

| Ex. | W | $R_1$ | $R_2$ | Y | $R_9$ | |
|---|---|---|---|---|---|---|
| 53 | —$CH_2CH_2$— | $OCH_3$ | 5-$OCH_3$ | —CH= | $OCH_3$ | oil |

$^1$H-NMR (CDCl$_3$): 8.36 (d, J = 2 Hz, 1H); 7.52 (dd, J = 2 + 8.6 Hz, 1H); 7.48 (d, J = 7.7 Hz, 1H); 7.32 (d, J = 8.6 Hz, 1H); 6.68–6.78 (m, 3H); 6.26 (d, J = 7.7 Hz); 3.80 (s, 3H); 3.79 (s, 3H); 3.74 (s, 3H); 2.90–3.04 (m, 4H).

The starting materials may be prepared in the following manner:
A) 5-[2-(2,5-Dimethoxyphenyl)ethenyl]-2-acetylamino Benzoic Acid Methylester 4.1 mmol of n-butyllithium (0.4 ml of 1.6 M solution in hexane) are added at −40° to a solution of 412 mg of diisopropylamine in 30 ml of dry tetrahydrofuran. After stirring for 30 minutes 672 mg of 2,5-dimethoxybenzyl-triphenylphosphonium bromide are added at this temperature. The suspension is stirred for another 30 minutes, cooled to −70° and treated with 300 mg of 2-acetylamino-5-formyl-benzoic acid methylester in 8 ml of absolute tetrahydrofuran. The mixture is stirred for one hour at −70° and for two hours at room temperature and then poured onto aqueous ammonium chloride solution. Extraction with ethyl acetate and evaporation yields a crude product, which is subjected to silica gel chromatography (hexane/ethyl acetate =9/1) to obtain the title compound as a mixture of the E- and Z-isomers.

$^1$H-NMR(CDCl$_3$): 11.05 (s, 1H E-isomer); 11.00 (s, 1H Z-isomer); 8.72 (d, J=8.8 Hz, 1H E-isomer); 8.52 (d, J=8.8 Hz, 1H Z-isomer); 8.16 (d, J=2.2 Hz, 1H E-isomer); 7.95 (d, J=2.2 Hz, 1H Z-isomer); 7.74 (dd, J=2.2+8.8 Hz, 1H E-isomer); 7.42 (dd, J=2.2+8.8 Hz, 1H Z-isomer); 7.41 (d, J=16.4 Hz, 1H E-isomer); 7.14 (d, J=2.6 Hz, 1H E-isomer); 7.05 (d, J=16.4 Hz, 1H E-isomer); 6.72–6.89 (m); 6.67 (d, J=12.2 Hz, 1H Z-isomer); 6.55 (d, J=12.2 Hz, 1H Z-isomer); 3.97 (s, 3H E-isomer); 3.87 (s); 3.83 (s, 3H E-isomer); 3.78 (s, 3H Z-isomer); 3.59 (s, 3H Z-isomer); 2.25 (s, 3H E-isomer); 2.22 (s, 3H Z-isomer).

B) (E)-5-[2-(2,6-Dimethoxyphenyl)ethenyl]-2-acetylamino Benzoic Acid Methylester The title substance is obtained analogously as described under A)

$^1$H-NMR(CDCl$_3$): 11.07 (s, 1 H); 8.68 (d, J=8.8 Hz, 1H); 8.13 (d, J=2.2 Hz, 1H); 7.76 (dd, J=2.2+8.8 Hz, 1H); 7.54 (d, J=16.6 Hz, 1H); 7.41 (d, J=16.6 Hz, 1H); 7.18 (t, J=8.3 Hz, 1H); 6.60 (d, J=8.3 Hz, 2H); 3.96 (s, 3H); 3.91 (s, 6H); 2.25 (s, 3H).

C) (E/Z)-5-[2-(2,5-Dimethoxyphenyl)ethenyl]-2-acetylamino-benzoic Acid Butylester The title substance is obtained analogously as described under A)

$^1$H-NMR(CDCl$_3$): 11.10 (s, 1H E-isomer); 11.06 (s, 1H Z-isomer); 8.70 (d, J=8.8 Hz, 1H E-isomer); 8.54 (d, J=8.8 Hz, 1H Z-isomer); 8.12 (d, J=2.2 Hz, 1H E-isomer); 7.96 (d, J=2.2 Hz, 1H Z-isomer); 7.74 (dd, J=2.2+8.8 Hz, 1H E-isomer); 7.42 (dd, J=2.2+8.8 Hz, 1H Z-isomer); 7.41 (d, J=16.4 Hz, 1H E-isomer); 7.14 (d, J=2.6 Hz, 1H E-isomer); 7.05 (d, J=16.4 Hz, 1H E-isomer); 6.72–6.89 (m); 6.67 (d, J=12.2 Hz, 1H Z-isomer); 6.55 (d, J=12.2 Hz, 1H Z-isomer); 4.36 (t, J=6.5 Hz, 2H E-isomer); 4.23 (t, J=6.5 Hz, 2H Z-isomer); 3.86 (s, 3H E-isomer); 3.82 (s, 3H E-isomer); 3.77 (s, 3H Z-isomer); 3.58 (s, 3H Z-isomer); 2.24 (s, 3H E-isomer); 2.21 (s, 3H Z-isomer); 1.20–1.85 (m); 1.02 (t, J=7.3 Hz, 3H E-isomer); 0.96 (t, J=7.3 Hz, 3H Z-isomer).

D) 6-[2-(2,5-Dimethoxyphenyl)ethynyl]-4-ethyl-quinazoline a) 6-Iodo-4-ethyl-quinazoline 154 mg of sodium are dissolved in 20 ml of dry methanol and treated with 1.2 g of 4-chloro-6-iodo-quinazoline. The mixture is heated to reflux for 1 hour, and then the solvent is distilled off. The residue is partitioned between aqueous pH7 buffer solution and ethyl acetate. The aqueous layer is extracted with ethyl acetate, and the combined organic extracts are dried over magnesium sulfate and evaporated in vacuo. The residue is dissolved in cyclohexane/ethyl acetate (1/1) and filtered over silica gel. The title compound is obtained as slightly yellowish crystals after evaporation of the solvent. mp: 110–113°.

b) 6-[2-(2,5-Dimethoxyphenyl)ethynyl]-4-ethyl-quinazoline

Argon is passed through a solution of 200 mg of 6-iodo-4-methoxy-quinazoline in 12 ml of dry dimethylformamide for 15 minutes. Then 40 mg of tetrakis(triphenylphosphine)-palladium, 113 mg of (2,5-dimethoxyphenyl)acetylene, 11 mg of copper(I)iodide and 220 mg of triethylamine are added, and the mixture is heated to 60° for 2 hours. The solvent is distilled off in vacuo and the residue partitioned between water and ethyl acetate. The organic layer is separated, dried and concentrated in vacuo. The pure title compound is obtained after chromatography (silica gel, cyclohexane/ethyl acetate=2/1) as colourless crystals. mp: 103–105°.

Analogously as described in D) the following compounds of formula IIb (E–Q) are obtained:
E) 6-[2-(2,5-Dimethoxyphenyl)ethynyl]quinazolin4-one, mp: 180–183°
F) 6-[2-(2,6-Dimethoxyphenyl)ethynyl]-4-methoxy-quinazoline, mp: 140–142°
G) 6-[2-(2,5-Dimethoxyphenyl)ethynyl]-4-ethoxy-quinazoline, mp: 75–77°
H) 6-[2-(2,6-Dimethoxyphenyl)ethynyl]quinazolin-4-one, mp: 219–221°
I) 6-[2-(2-Benzyloxy-5-methoxyphenyl)ethynyl]methoxy-quinazoline, mp: 112–114°
J) 6-[2-(2,5-Dimethoxyphenyl)ethynyl]-methyl-quinazoline, mp:113–116°
K) 6-[2-(2,5-Dimethoxyphenyl)ethynyl]-4-methoxy-quinazoline, mp:103–105°
L) 6-[12-(2,5-Diethylphenyl)ethynyl]-4-ethyl-quinazoline, mp: 56°
M) 6-[2-(2,6-Dimethoxyphenyl)ethynyl]-4-ethyl-quinazoline, mp: 155–157°
N) 5-[2-(2,5-Dimethoxyphenyl)ethynyl]-2-amino-benzamide $^1$H-NMR(d$_6$-DMSO:): 7.90 (br.s, 1H); 7.75 (d, J=2 Hz, 1H); 7.27 (dd, J=2+8.5 Hz, 1H); 7.15 (br.s, 1H); 6.93–7.05 (m, 4H); 6.90 (dd, J=3+8.8 Hz, 1H); 6.71 (d, J=8.5 Hz, 1H); 3.79 (s, 3H); 3.72 (s, 3H).

O) 6-[2-(2,5-Diethoxyphenyl)ethynyl]-4-ethyl-quinazoline $^1$H-NMR (CDCl$_3$): 9.21 (s, 1H); 8.30 (m, 1H); 7.93–8.04 (m, 2H); 7.08 (m, 1H); 6.82–7.1 (m, 2H); 4.13 (qua, J=7 Hz, 2H); 4.02 (qua, J=7 Hz, 2H); 3.32 (qua, J=7.5 Hz, 2H); 1.50 (t, J=7 Hz, 3H); 1.48 (t, J=7.5 Hz, 3H); 1.41 (t, J=7 Hz, 3H).

P) 6-[2-(S-Benzyloxy-2-methoxyphenyl)ethynyl]-4-methoxyquinazoline

¹H-NMR (CDCl₃): 8.81 (s, 1H); 8.37 (d, J=1.8 Hz, 1H); 7.96 (dd, J=1.8+8.6 Hz, 1H), 7.89 (d, J=8.6 Hz, 1H); 7.30–7.50 (m, 5H); 7.18 (d, J=3 Hz, 1H); 6.98 (dd, J=3+9 Hz, 1H); 6.85 (d, J=9 Hz, 1H); 5.05 (s, 2H); 6.20 (s, 3H); 3.90 (s, 3H).

Q) 6-[2-(2,5-Dimethoxyphenyl)]quinazoline mp: 100–102°

R) 4-Diacetylamino-6-[2-(2,5-dimethoxyphenyl)ethynyl]quinazoline a) 4-Amino-6-iodo-quinazoline 500 mg of 4-chloro-6-iodo-quinazoline are treated with 30 ml of aqueous ammonium hydroxide solution and heated to reflux for 2 hours. After cooling the precipitated title compound is filtered and dried.

¹H-NMR (d₆-DMSO): 8.66 (d, J=1.8 Hz, 1H), 8.4 (s, 1H), 8.02 (dd, J=1.8+8.7 Hz, 1H), 7.85 (br s, 2H), 7.45 (d, J=8.7 Hz, 1H).

b) 4-Diacetylamino-6-iodo-quinazoline

A mixture of 340 mg of 4-amino-6-iodo-quinazoline, 1 ml of pyridine, and 20 ml of acetic anhydride is heated to 80° for 1 hour. The cold mixture is poured onto ice/water, stirred vigorously and extracted with ethyl acetate. The combined organic extracts are dried over magnesium sulfate and concentrated in vacuo. The title compound is obtained by chromatographic purification on silica gel (ethyl acetate/cyclohexane=2/1).

¹H-NMR (CDCl₃): 9.36 (s, 1H), 8.22 (dd, J=1.9 +8.9 Hz, 1H), 8.17 (d, J=1.8 Hz, 1H), 7.90 (d, J=8.9 Hz, 1 H), 2.34 (s, 6H).

c) 4-Diacetylamino-6-[2-(2,5-dimethoxyphenyl)ethynyl]-quinazoline

The title substance is obtained analogously as described under C/b. ¹H-NMR (CDCl₃): 9.33 (s, 1H), 8.09 (dd, J=0.7+8.8 Hz, 1H), 8.04 (dd, J=1.65 +8.8 Hz, 1H), 7.95 (dd, J=0.7+1.65 Hz, 1H), 7.06 (d, J=2.9 Hz, 1H), 6.90 (dd, J=2.9+9 Hz, 1H), 6.82 (d, J=9 Hz, 1H), 3.86 (s, 3H), 3.76 (s, 3H), 2.30 (s, 6H).

S) 6-[2-(2,5-Dimethoxyphenyl)ethynyl]-4-methylamino-quinazoline a) 6-Iodo-4-methylamino-quinazoline Prepared analogously to the method described for the synthesis of 4-amino-6-iodo-quin-azoline. mp: 245°.

b) 6-[2-(2,5-Dimethoxyphenyl)ethynyl]-4-methylamino-quinazoline

The title substance is obtained analogously as described under D/b.

T) 6-[2-(2,5-Dimethoxyphenyl)ethynyl]-quinazoline

U) Diethyl {4-[2-(2,5-dimethoxyphenyl)ethyl]anilino}methylene-malonate

The mixture of 820 mg of 4-[(2,5-dimethoxyphenyl)ethyl]aniline and 690 mg of diethyl ethoxymethylene-malonate is heated to 95° for 2 hours. On cooling the product crystallises and is used without further purification.

¹H-NMR (CDCl₃): 10.98 (d, J=13.8 Hz, 1H), 8.51 (d, J=13.8 Hz,1H), 7.14–7.22 (m, 2H), 7.01–7.09 (m, 2H), 6.78 (d, J=8.7 Hz, 1 H), 6.70 (dd, J=3+8.7 Hz, 1H), 6.66 (d, J=3 Hz, 1H), 4.31 (qua, J=7.1 Hz, 2H), 4.24 (qua, J=7.1 Hz, 2H), 3.78 (s, 3H), 3.74 (s, 3H), 2.86 (s, 4H), 1.38 (t, J=7.1 Hz, 3H), 1.33 (t, J=7.1 Hz, 3H).

V) 5-(2,5-Dimethoxybenzyloxy)-2-formylaminobenzamide

A solution of 140 mg of 2-formylamino-5-hydroxybenzamide in 15 ml of dry dimethylformamide is treated subsequently with 160 mg of potassium carbonate and 180 mg of 2,5-dimethoxybenzylbromide. The mixture is stirred at room temperature for 4 hours, and then the solvent is distilled off in vacuo. The residue is partitioned between water and ethyl acetate, and the separated organic layer is dried over magnesium sulfate and evaporated in vacuo. Purification of the crude product thus obtained by silica gel chromatography (ethyl acetate) gives the title compound as colourless crystals. mp: 135–138°.

W) 3-(2,6-Dimethoxybenzyl)-6-hydroxy-3H-quinazolin-4-one 76 mg of sodium hydride (80% in mineral oil) are added to a suspension of 400 mg of 6-hydroxy-3H-quinazolin-4-one in 20 ml of dry dimethylformamide. After stirring for 30 minutes at room temperature, 560 mg of 2,6-dimethoxybenzylbromide are added, and stirring is continued overnight. The solvent is distilled off in vacuo, and the residue partitioned between aqueous pH7-buffer solution and ethyl acetate. The organic phase is separated, dried over magnesium sulfate and evaporated in vacuo. Silica gel chromatography yields a minor amount of the N,O-bis-alkylated product followed by the pure title compound as colourless crystals. mp: 243–245°.

X) 3-(2,5-Dimethoxybenzyl)-6-hydroxy-3H-quinazolin-4-one

Prepared analogously as described under V). mp: 203°.

Y) 6-Hydroxy-4-methoxyquinazoline

A mixture of 200 mg of 6-hydroxy-3H-quinazolin-4-one and 5 ml of phosphorylchloride is heated to reflux for 2 hours. The excess phosphorylchloride is distilled off in vacuo and the residue is taken up in a solution of sodium methoxide (prepared from 80 mg sodium) in dry methanol. After refluxing for 2 hours the solvent is distilled off and the residue is partitioned between aqueous ph7-buffer solution and ethyl acetate. The organic phase is separated, dried over magnesium sulfate and evaporated in vacuo. The crude product is directly used in the next reaction or purified by chromatography on silica gel.

¹H-NMR (d₆-DMSO): 10.25 (br.s, 1H); 8.61 (s, 1H); 7.79 (d, J=9 Hz, 1H); 7.45 (dd,J=2.8+9 Hz, 1H); 7.32 (d,J=2.8 Hz, 1H); 4.09 (s,3H).

The compounds of this invention possess advantageous chemotherapeutical properties and exhibit on local, systemic or oral application antiproliferative/antiinflammatory and/or anticancer activity. These activities can be shown in the following tests, wherein the following abbreviations are used:

BSA=bovine serum albumin
HaCaT=the cell line known as "human adult calcium temperature"
HeLa-O=tumor cell line from human cervix
A375=human melanoma cell line
A549=human lung carcinoma cell line
MDA-MB-231=human breast carcinoma cell line
SW-480=human colon carcinoma cell line
DMEM=Dulbecco's modified eagle medium
EGF=epidermal growth factor
FCS=fetal calf serum
TGFα=transforming growth factor a
BSA=bovine serum albumin
MDA-MB-435=human breast carcinoma cell line
HT-29=human colon carcinoma cell line 1. Inhibition of Proliferation in the Human Keratinocyte Cell Line HaCaT HaCaT cells, a spontaneously transformed, TGFα- and EGF-receptor positive non-tumorigenic human keratinocyte cell line with highly preserved phenotypic differentiation characteristics of normal keratinocytes (Boukamp et al., J. Cell. Biol. 106: 761–771[1988]), are cultivated in DMEM medium supplemented with 2.2 g/l NaHCO₃, 0.11 g/l sodium pyruvate, 15 mM Hepes, 5% fetal calf serum (FCS), penicillin (100 U/ml), streptomycin (100 μg/ml), and glutamine (to increase the final concentration by 4 mM). For the proliferation assay, cells are detached by trypsinization, suspended in fresh medium, and seeded into 96-well microtiter plates at 2000–4000 cells/0.2 ml/well. After 24 hours the medium is replaced with fresh medium containing graded concentrations of test compound. After 3–4 days of incubation, the extent of cellular proliferation is measured by a colorimetric assay using sulforhodamine B (Skehan et al., J. Natl. Cancer Inst. 82: 1107–1112 [1990]). The results represent the average ∓ standard deviation of three measurments.

In this test the compounds of the invention inhibit cell proliferation with $IC_{50}$-values ranging from about 0.003 μM to about 3 μM.

2. Inhibition of Tumor Cell Proliferation:

Tumor cell lines, for example A375, A549, HeLa-O, MDA-MB-231, SW-480, MDA-MB 435 and HT-29, available from American Type Culture Collection, are grown in medium supplemented with 5 to 10% heat inactivated (56° C./30 mim) FCS and antibiotics. At the time of 60–90% confluence the cells are harvested, trypsinized, suspended in fresh growth medium and seeded into 96 well cell culture plates at concentrations ranging between 1000 and 5000 cells/well. Cells are grown for 3–4 days in a final volume of 0.2 ml/well, at 37° C. in an humidified incubator equilibrated with 5% $CO_2$, in the presence of graded concentrations of test compound. Extent of cellular proliferation is measured by a colorimetric assay using MTS (Buttke et al., J.Immunol. Meth. 157: 233–240 [1993]) for cells growing in suspension or by sulforhodamine B for adherent cells. In this experimental system the compounds of this invention inhibit cell proliferation with $IC_{50}$ ranging between 0.01 and 5 μM.

The compounds of the invention are therefore indicated for use as antiproliferative/antiinflammatory and anticancer agents in the treatment of proliferative/inflammatory disorders and cancer such as in suppression of neoplastic diseases, e.g. inflammatory/proliferative skin diseases and skin cancer, and autoimmune diseases, such as: psoriasis, atopical dermatitis, contact dermatitis and related eczematous dermatitises, seborrheic dermatitis, Lichen planus, Pemphigus, bullous Pemphigoid, Epidermolysis bullosa, urticaria, angioedemas, vasculitides, erythemas, cutaneous eosinophilias, Lupus erythematosus and Alopecia areata.

For this use the dosage to be used will vary, of course, depending e.g. on the particular compound employed, the mode of administration and the treatment desired. However, in general, satisfactory results are obtained when the compounds are administered at a daily dosage of from about 1 mg/kg to about 30 mg/kg animal body weight, suitably given in divided doses two to four times daily. For most large mammals the total daily dosage is from about 70 mg to about 2000 mg, conveniently administered, for example, in divided doses up to four times a day or in retard form. Unit dosage forms comprise, for example, from about 17.5 mg to about 1000 mg of the compounds in admixture with at least one solid or liquid pharmaceutically acceptable carrier or diluent.

The compounds of the invention may be administered in similar manner to known standards for use in such indications. The compounds may be admixed with conventional chemotherapeutically acceptable carriers and diluents and, optionally, further excipients, and administered e.g. orally in such forms as tablets and capsules.

Alternatively, the compounds may be administered topically in such conventional forms as ointments or creams, parenterally or intravenously. The concentrations of the active substance will, of course vary depending e.g. on the compound employed, the treatment desired and the nature of the form. In general, however, satisfactory results are obtained, e.g. in topical application forms at concentrations of from about 0.05 to about 5%, particularly from about 0.1 about 1% by weight.

Pharmaceutical compositions comprising a compound of the invention together with at least one pharmaceutically acceptable carrier or diluent also form part of the invention, as well as a process for the preparation thereof by mixing together with at least one pharmaceutically acceptable carrier or diluent. The invention also comprises the compounds of the invention for use as pharmaceuticals, especially in the prevention or treatment of inflammatory and proliferative skin illnesses and cancer.

The invention further comprises a method of prevention or treatment of inflammatory and proliferative skin diseases and cancer, which comprises administering a therapeutically effective amount of a compound of the invention to a subject in need of such treatment.

The compounds of the invention of formula Is and especially the compounds of formula Iss are particularly preferred.

The compounds of example 6, 16 and 17, namely 6-[2-(2,5- dimethoxyphenyl)ethyl]-4-ethyl-quinazoline and, respectively, the corresponding 4-methoxy and 4-methyl compounds, are the most preferred compounds as antiproliferative/antiinflammatory and anticancer agents, especially the compound of Example 6. It has, for example, been determined that in the above test 1 these 3 compounds have an $IC_{50}$ of about 10 nM, in the above test 2 an $IC_{50}$ between 10 and 200 nM.

I claim:

1. Compounds of formula I

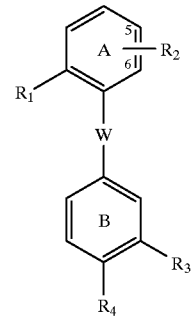

wherein $R_1$ and $R_2$ are the same or different and represent hydroxy, $C_{1-12}$alkoxy, acyloxy, $C_{1-12}$alkyl or acyl, whereby $R_2$ is in the 5- or 6-position, with the proviso that $R_1$ and $R_2$ are not simultaneously hydroxy or acyloxy, and W represents —$CH_2CH_2$—, —CH=CH—, —$CH_2O$— or —$CH_2NR_5$—, whereby the heteroatom adheres to ring B and $R_5$ represents hydrogen, $C_{1-12}$alkyl or acyl, $R_3$ and $R_4$ form together with the adjacent ring B a condensed ring system of formula

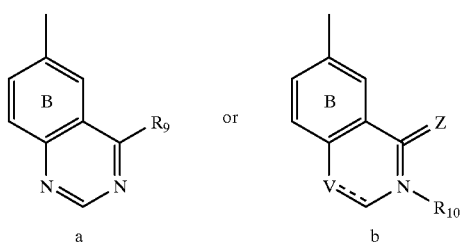

wherein the symbol ==== represents a single or double bond, $R_9$ represents hydrogen, $C_{1-12}$alkylthio, $C_{1-12}$alkyl, $(C_{1-12}$alkoxy)carbonyl, acyl, amino, acylamino, diacylamino, $C_{1-12}$alkylamino, $(diC_{1-12}$alkyl)amino, cyano, hydroxy, $C_{1-12}$alkoxy or mercapto, $R_{10}$ represents hydrogen, $C_{1-12}$alky, acyl or dialkoxybenzyl independently of 1 to 4 carbon atoms in the alkoxy part thereof, Z represents O or S and V represents NH, if the symbol ==== represents a single bond, and N, if the symbol ==== represents a double bond, with the proviso that, if $R_9$ represents hydroxy or mercapto and Y represents N, the compounds exist predominantly in the tautomeric form of formula It

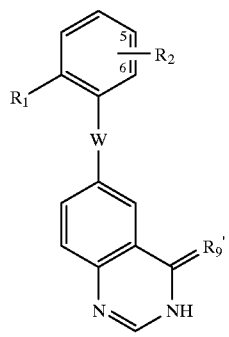

wherein $R_9'$ represents O or S, in free form or, where such forms exist, in salt form, and each said acyl independently represents the residue of a $C_{1-4}$alkyl, arylalkyl or aryl carboxylic acid.

2. Compounds according to claim 1 of formula

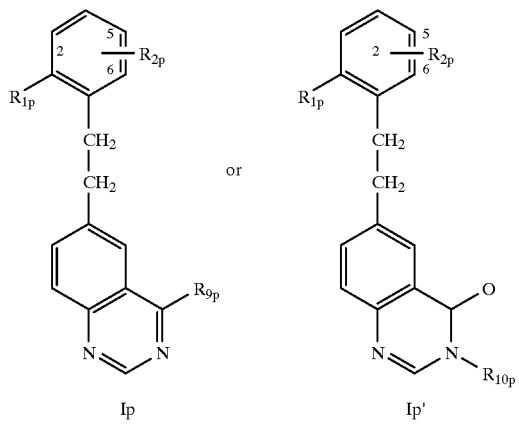

wherein $R_{1p}$ and $R_{2p}$ are the same or different and represent hydroxy, $C_{1-12}$alkoxy, acyloxy, $C_{1-12}$alkyl or acyl, whereby $R_{2p}$ is in the 5- or 6-position, with the proviso that $R_{1p}$ and $R_{2p}$ are not simultaneously hydroxy or acyloxy, $R_{9p}$ represents hydrogen, $C_{1-12}$ alkyl, $(C_{1-12}$ alkoxy)carbonyl, acyl, amino, acylamino, diacylamino, $C_{1-12}$alkylamino $(diC_{1-12}$ alkyl) amino, cyano, $C_{1-12}$alkoxy or hydroxy, and $R_{10p}$ represents hydrogen, $C_1$–$C_{12}$ alkyl or acyl, with the proviso that, if $R_{9p}$ represents hydroxy, the compounds exist predominantly in the tautomeric form of formula Ip'

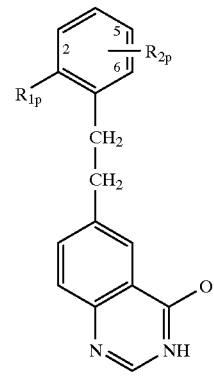

in free form, or where such forms exist, in salt form.

3. Compounds according to claim 1 of formula Is

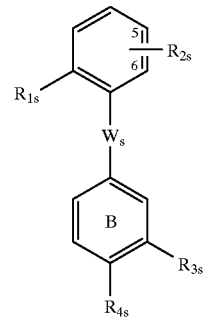

wherein
$R_{1s}$ is hydroxy, alkyl of 1 to 4 carbon atoms or alkoxy of 1 to 4 carbon atoms;
$R_{2s}$ is hydroxy or alkoxy of 1 to 4 carbon atoms and is in the 5- or 6-position, whereby $R_{1s}$ and $R_{2s}$ are not simultaneously hydroxy; and
$W_s$ is —$CH_2CH_2$—, —$CH_2NH$—, —$CH_2O$— or —$CH$=$CH$—, whereby the nitrogen or oxygen atom is bound to ring B; and
$R_{3s}$ and $R_{4s}$ together with ring B form a condensed ring system of formula

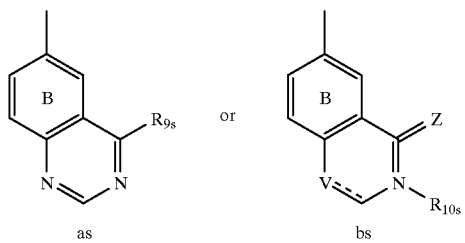

wherein the symbol ==== is a single or a double bond;

$R_{9s}$ is hydrogen, alkylthio of 1 to 4 carbon atoms, alkyl of 1 to 4 carbon atoms, amino, diacetylamino, alkylamino of 1 to 4 carbon atoms, hydroxy, alkoxy of 1 to 4 carbon atoms or mercapto;

$R_{10s}$ is hydrogen, alkyl of 1 to 4 carbon atoms or dialkoxybenzyl independently of 1 to 4 carbon atoms in the alkoxy parts thereof; and Z and V are as defined in claim 1, with the proviso that, if $R_{9s}$ is hydroxy or mercapto, then the compounds exist predominantly in the tautomeric form of formula Its

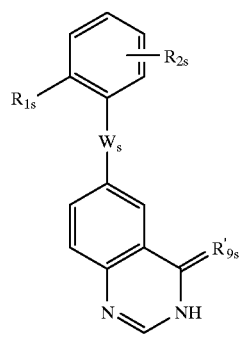

Its wherein $R'_{9s}$ is O or S, in free form or, where such forms exist, in salt form.

4. Compounds according to claim 1 of formula

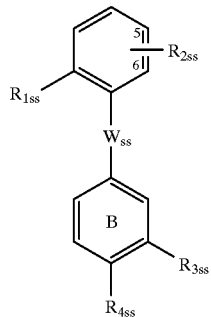

Iss wherein $R_{1ss}$ is hydroxy, alkyl of 1 or 2 carbon atoms or alkoxy of 1 or 2 carbon atoms;

$R_{2ss}$ is hydroxy or alkoxy of 1 or 2 carbon atoms and is in the 5- or 6-position, whereby $R_{1ss}$ and $R_{2ss}$ are not simultaneously hydroxy;

$W_{ss}$ is —CH$_2$CH$_2$—, —CH$_2$NH—, —CH$_2$O— or —CH=CH—, whereby the nitrogen or oxygen atom is bound to ring B; and $R_{3ss}$ and $R_{4ss}$ together with ring B form a condensed ring system of formula

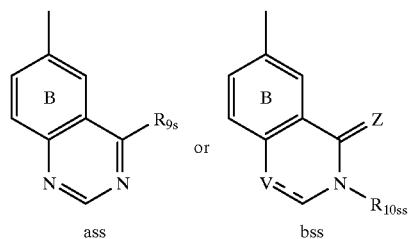

wherein the symbol ==== is a single or a double bond;

$R_{9S}$ is hydrogen, alkylthio of 1 to 4 carbon atoms, alkyl of 1 to 4 carbon atoms, amino, diacetylamino, alkylamino of 1 to 4 carbon atoms, hydroxy, alkoxy of 1 to 4 carbon atoms or mercapto;

$R_{10SS}$ is hydrogen, methyl, 2,5-dimethoxybenzyl or 2,6-dimethoxybenzyl; and

Z and V are as defined in claim 4;

whereby, if $R_{9S}$ is hydroxy or mercapto, then the compounds exist predominantly in the tautomeric form of formula

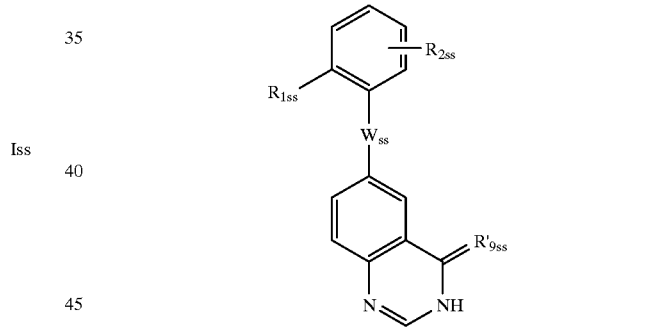

Itss wherein $R_{1SS}$ and $R_{2SS}$ are as defined in this claim and $R'_{9SS}$ is oxygen or sulfur, in free form or, where such forms exist, in salt form.

5. The compound 6-[2-(2,5-dimethoxyphenyl)ethyl]-4-ethyl-quinazoline, or 6-[2-(2,5-dimethoxyphenyl)ethyl]-4-ethoxy-quinazoline, or 6-[2-(2,5-dimethoxyphenyl)ethyl]-4-methyl-quinazoline, in free form or, where such forms exist, in salt form.

6. The compound 6-[2-(2,5-dimethoxyphenyl)ethyl]-4-ethyl-quinazoline.

7. Process for the preparation of compounds of formula I as defined in claim 1, comprising a) for the preparation of compounds of formula Ia and Ib

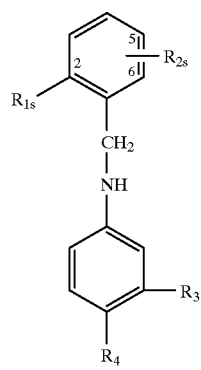

Ib wherein $R_1$, $R_2$, $R_3$, and $R_4$ are as defined in claim 1, reducing a compound of formula IIa, IIb or IIc

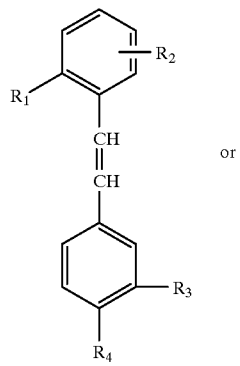

IIa or

IIb or

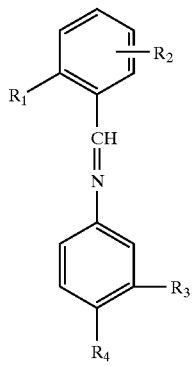

IIc wherein are as defined in claim 1, whereby in this reaction functional groups may be protected by suitable protecting groups, which may be removed subsequent to the reaction and recovering thus obtained compounds of formula I in free form or, where such forms exist, in salt form.

8. A pharmaceutical composition comprising a compound according to claim 1 together with at least one pharmaceutically acceptable carrier or diluent.

9. A process for the preparation of a pharmaceutical composition according to claim 8 comprising mixing a compound according to claim 1 together with at least one pharmaceutically acceptable carrier or diluent.

10. A method of inhibiting cell proliferation comprising administering to a subject in need of such inhibiting an effective amount of a compound according to claim 1.

11. A method of treatment of psoriasis comprising administering a therapeutically effective amount of a compound according to claim 1 to a subject in need of such treatment.

* * * * *

UNITED STATES PATENT AND TRADEMARK OFFICE
CERTIFICATE OF CORRECTION

PATENT NO. : 5,990,116
DATED : November 23, 1999
INVENTOR(S) : Peter Nussbaumer

It is certified that error appears in the above-identified patent and that said Letters Patent is hereby corrected as shown below:

Claim 6, line 2, after "quinazoline" insert --and salts thereof--.

Insert new claim 12.

12. The compound, 6-[2-(2,5-dimethoxyphenyl)ethyl]-4-methoxy-quinazoline and salts thereof, according to claim 1.--

Signed and Sealed this

Sixteenth Day of May, 2000

Attest:

Q. TODD DICKINSON

*Attesting Officer*     *Director of Patents and Trademarks*